United States Patent
Heflin et al.

(10) Patent No.: US 12,156,683 B2
(45) Date of Patent: Dec. 3, 2024

(54) HYDRAULIC GROWING ROD

(71) Applicant: University of Utah Research Foundation, Salt Lake City, UT (US)

(72) Inventors: John Heflin, Salt Lake City, UT (US); T. Wade Fallin, Hyde Park, UT (US); Zackery Evans, Woods Cross, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 0 days.

(21) Appl. No.: 17/899,464

(22) Filed: Aug. 30, 2022

(65) Prior Publication Data
US 2023/0069132 A1 Mar. 2, 2023

Related U.S. Application Data

(60) Provisional application No. 63/238,299, filed on Aug. 30, 2021.

(51) Int. Cl.
*A61B 17/70* (2006.01)
*A61M 5/168* (2006.01)
*F04B 43/04* (2006.01)

(52) U.S. Cl.
CPC ..... *A61B 17/7098* (2013.01); *A61M 5/16854* (2013.01); *F04B 43/046* (2013.01)

(58) Field of Classification Search
CPC ............. A61B 17/7097; A61B 17/7098; F04B 43/043; F04B 43/046
See application file for complete search history.

(56) References Cited

U.S. PATENT DOCUMENTS

| | | | |
|---|---|---|---|
| 5,037,431 A * | 8/1991 | Summers | A61B 17/3203 606/167 |
| 5,350,379 A * | 9/1994 | Spievack | A61B 17/7216 606/63 |
| 5,356,411 A | 10/1994 | Spievack | |
| 6,565,576 B1 | 5/2003 | Stauch et al. | |
| 10,052,134 B2 * | 8/2018 | Kercher | A61B 17/7014 |
| 2006/0069447 A1 | 3/2006 | DiSilvestro et al. | |
| 2009/0259319 A1 | 10/2009 | DiSilvestro et al. | |
| 2009/0281542 A1 * | 11/2009 | Justis | A61B 17/7017 606/192 |
| 2013/0204376 A1 | 8/2013 | DiSilvestro et al. | |
| 2021/0259748 A1 * | 8/2021 | Mullaney | A61B 17/72 |

* cited by examiner

*Primary Examiner* — Si Ming Ku
(74) *Attorney, Agent, or Firm* — David Meibos; Maywood IP Law

(57) ABSTRACT

A bone implant system may include a plurality of bone anchors, a superior rod attachable to a superior portion of a bone via the bone anchors, and an inferior rod attachable to an inferior portion of the bone via the bone anchors. The superior rod may have a superior end, and the inferior rod may have an inferior end. The superior rod may telescopically engage the inferior rod such that a cavity is present within at least one of the superior rod and the inferior rod and such that a length of the combined superior and inferior rods, measured between the superior end and the inferior end, is adjustable. The cavity may contain a micropump and a chamber. The micropump may be configured to expel fluid into the chamber to urge the length to increase.

25 Claims, 6 Drawing Sheets

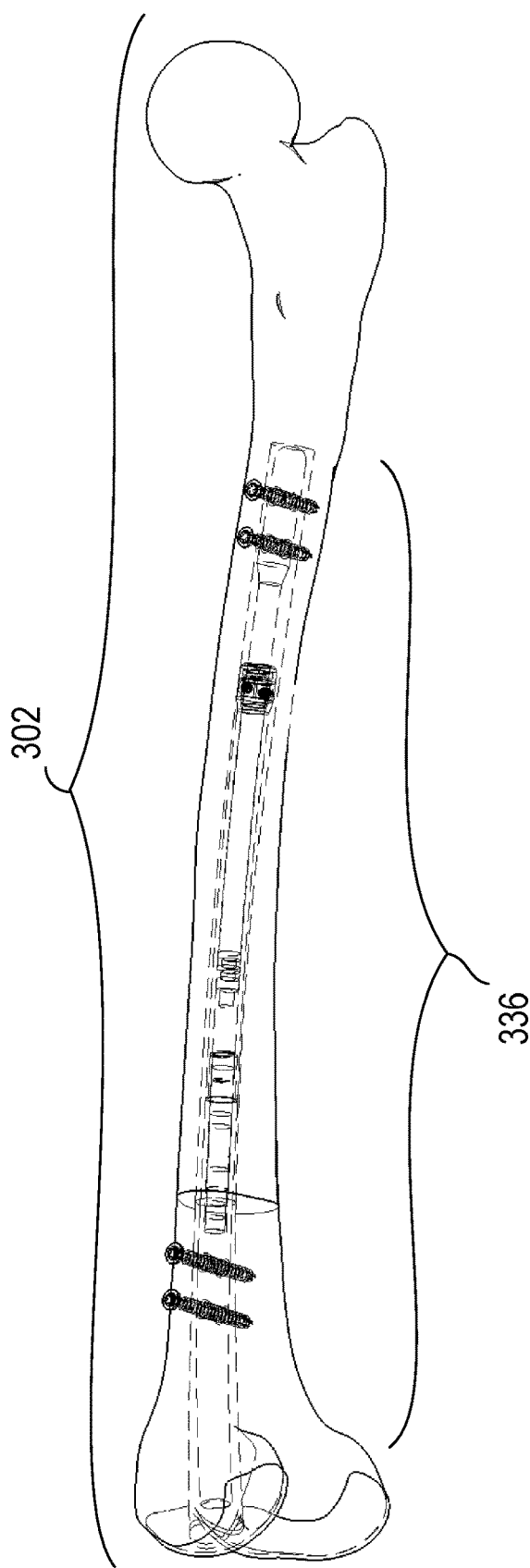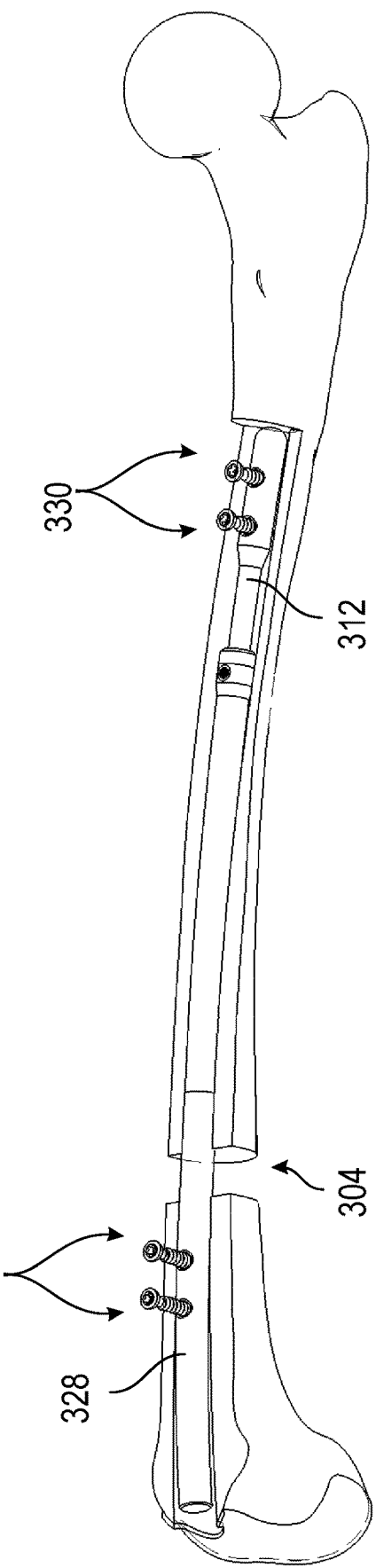

HYDRAULIC GROWING ROD

CROSS-REFERENCE TO RELATED APPLICATIONS

The present application claims the benefit of U.S. Provisional Patent Application No. 63/238,299 filed on Aug. 30, 2022, entitled "Hydraulic Growing Rod," which is incorporated herein by reference in its entirety.

TECHNICAL FIELD

The present disclosure relates to orthopedic growing rod devices, systems, and methods. More specifically, the present disclosure relates to hydraulically actuated growing rods that can change the spacing between a first bone portion and a second bone portion.

BACKGROUND

Scoliosis is a medical condition in which a person's spine is abnormally curved and/or rotated. It is typically classified as congenital (caused by anomalies at birth), neurologic (occurring secondary to central nervous system disorders), or idiopathic (developing over time without definite cause). Idiopathic scoliosis is further sub-classified according to the age at which it occurs, earlier onset being associated with worse prognosis. Treatment of children with progressive scoliosis occurring at a young age is a difficult problem. Left untreated, progressive curves can produce significant deformity leading to deleterious effects on the developing heart and lungs resulting in a shortened lifespan.

Standard treatment for scoliosis includes spinal fusion surgery. This has limited use in younger children because of the potential alteration or cessation of spinal growth, which in turn can have adverse effects on axial growth, chest wall development, and lung development.

There are known methods to treat spinal deformities in the developing child that avoid spinal fusion. These include external bracing and surgery without spinal fusion. However, most early onset scoliosis is rapidly progressive and largely resistant to bracing, and compliance with brace-wearing regimens is generally very poor, which often makes surgical correction the preferred option.

Known non-fusion, growth-preserving surgical procedures include the placement of special spinal instrumentation known as growing rods. Growing rods are devices placed surgically within a patient's back that provide internal bracing in an effort to limit curve progression. Some known growing rod systems have dual, parallel growing rods that are secured to vertebrae of a spine above and below the deformity, thus spanning the curve being addressed. The growing rods may be secured to the spine at foundation sites by mounting hardware (e.g., including mounting clamps, screws, and/or hooks) to form fixation constructs. Typically, two rods are implanted in a parallel arrangement with one on each lateral side of the spine. Each rod is typically composed of two independent rod segments that are longitudinally coupled together using tandem connectors. This configuration allows the rods to be longitudinally adjusted (e.g., telescopically) at regular intervals to provide an overall increase in length.

Growing rod placement is an accepted technique that allows correction of deformity without preventing normal axial growth of the spine. This method requires frequent periodic lengthening of the rod system to adjust for longitudinal growth of the spine as the patient matures. Lengthening is performed by loosening the connectors, using a distraction device to push the rod segments apart until the appropriate amount of lengthening has been achieved, and retightening the connectors.

Known growing rod devices have a number of drawbacks, including (1) the number and invasiveness of follow-up surgical treatments needed to elongate the system in tandem with the child's growth, (2) the reliability of systems and parts used to permit growth, and (3) the space required by the implanted system. Further, many known systems are not usable outside the spine.

SUMMARY

The various spinal implant devices, systems, and methods of the present disclosure have been developed in response to the present state of the art, and in particular, in response to the problems and needs in the art that have not yet been fully solved by currently available bone implant devices, systems, and methods. In some embodiments, the bone implant devices, systems, and methods of the present disclosure may serve to provide (1) fewer/less invasive treatments to elongate the system, (2) enhanced reliability, and/or (3) a more compact system that presents less discomfort, tissue disruption, and healing time for the patient. Such bone implant systems may be used for the spine and/or other bones in the body.

According to one embodiment, a bone implant system may have a plurality of bone anchors, a superior rod attachable to a superior portion of a bone via the bone anchors, and an inferior rod attachable to an inferior portion of the bone via the bone anchors. The superior rod may have a superior end, and the inferior rod may have an inferior end. The inferior rod may be movably coupled to the superior rod such that a length of the combined superior and inferior rods, measured between the superior end and the inferior end, is adjustable. The system may further have a chamber and a micropump configured to urge fluid to flow into the chamber to cause the length to increase.

The superior rod may telescopically engage the inferior rod such that a cavity is present within at least one of the superior rod and the inferior rod. The chamber may be within the cavity.

The micropump may be within the cavity and may include be a piezoelectric motor or a thermal phase change pump.

The bone implant system may further have an outlet check valve configured to permit flow of the fluid from the micropump to the chamber and restrict flow of the fluid from the chamber to the micropump.

The bone implant system may further have a reservoir and an inlet check valve configured to permit flow of the fluid from the reservoir to the micropump and restrict flow of the fluid from the micropump to the reservoir.

The bone implant system may further have a control system, operatively connected to the micropump, that is configured to control operation of the micropump.

The control system may have a wireless communication device configured to transmit and/or receive wireless signals.

The bone implant system may further have a control unit that is not configured to be implanted in a body of a patient. The control unit may have a first inductive coil. The control system may further have a second inductive coil configured to inductively receive electrical power from the first inductive coil.

The bone implant system may further have a sensor operatively connected to provide sensor data to the control system. The control system may be configured to control the micropump based on the sensor data.

The sensor data may be indicative of a pressure of the fluid and/or a displacement of the superior rod relative to the inferior rod.

The inferior rod may be movably coupled to the superior rod such that the superior rod moves along an arcuate pathway relative to the inferior rod.

According to one embodiment, a bone implant system may have a plurality of bone anchors, a superior rod attachable to a superior portion of a bone via the bone anchors, and an inferior rod attachable to an inferior portion of the bone via the bone anchors. The superior rod may have a superior end and the inferior rod may have an inferior end. The inferior rod may be movably coupled to the superior rod such that a length of the combined superior and inferior rods, measured between the superior end and the inferior end, is adjustable along an arcuate axis. The system may further have a pump positioned on the arcuate axis and configured to pressurize a fluid to urge the length to increase.

The superior rod may telescopically engage the inferior rod such that a cavity is present within at least one of the superior rod and the inferior rod. The bone implant system may further have a chamber, positioned within the cavity, into which the pump expels the fluid to urge the length to increase in response to pressurization of the fluid.

The pump may be within the cavity. The pump may be a micropump that includes a piezoelectric motor and/or a thermal phase change pump.

The bone implant system may further have an outlet check valve configured to permit flow of the fluid from the pump to the chamber and restrict flow of the fluid from the chamber to the pump.

The bone implant system may further have a reservoir and an inlet check valve configured to permit flow of the fluid from the reservoir to the pump and restrict flow of the fluid from the pump to the reservoir.

The bone implant system may further have a control system, operatively connected to the pump, that is configured to control operation of the pump.

The control system may have a wireless communication device configured to transmit and/or receive wireless signals.

The bone implant system may further have a control unit that is not configured to be implanted in a body of a patient, the control unit comprising a first inductive coil. The control system may further have a second inductive coil configured to inductively receive electrical power from the first inductive coil.

The bone implant system may further have a sensor operatively connected to provide sensor data to the control system. The control system may be configured to control the pump based on the sensor data.

The sensor data may be indicative of a pressure of the fluid and/or a displacement of the superior rod relative to the inferior rod.

The inferior rod may be movably coupled to the superior rod such that the superior rod moves along an arcuate pathway relative to the inferior rod.

According to one embodiment, a bone implant system may have a plurality of bone anchors, a superior rod attachable to a superior portion of a bone via the bone anchors, and an inferior rod attachable to an inferior portion of the bone via the bone anchors. The superior rod may have a superior end and the inferior rod may have an inferior end. The inferior rod may be movably coupled to the superior rod such that a length of the combined superior and inferior rods, measured between the superior end and the inferior end, is adjustable. The system may further have a chamber, a pump configured to urge fluid to flow into the chamber to cause the length to increase, and an outlet check valve configured to permit flow of the fluid from the pump to the chamber to allow the length to increase and restrict flow of the fluid from the chamber to the pump to restrict reduction in the length.

The bone implant system may further have a reservoir, an inlet check valve configured to permit flow of the fluid from the reservoir to the pump and restrict flow of the fluid from the pump to the reservoir, and an outlet check valve configured to permit flow of the fluid from the pump to the chamber and restrict flow of the fluid from the chamber to the pump.

The bone implant system may further have a control system, operatively connected to the pump, that is configured to control operation of the pump. The control system may have a wireless communication device configured to transmit and/or receive wireless signals.

The superior rod may telescopically engage the inferior rod such that a cavity is present within at least one of the superior rod and the inferior rod. The pump and the chamber may be within the cavity. The inferior rod may be movably coupled to the superior rod such that the superior rod moves along an arcuate pathway relative to the inferior rod.

The pump may include a micropump that includes a piezoelectric motor and/or a thermal phase change pump.

These and other features and advantages of the present disclosure will become more fully apparent from the following description and appended claims or may be learned by the practice of the devices, systems, and methods set forth hereinafter.

BRIEF DESCRIPTION OF THE DRAWINGS

Exemplary embodiments of the present disclosure will become more fully apparent from the following description taken in conjunction with the accompanying drawings. Understanding that these drawings depict only exemplary embodiments and are, therefore, not to be considered limiting of the scope of the present disclosure, the exemplary embodiments of the present disclosure will be described with additional specificity and detail through use of the accompanying drawings in which:

FIG. 9 is a perspective view of a bone implant system mounted in a human femur, according to one embodiment.

FIG. 10 is a partial cutaway view of the bone implant system of FIG. 9, mounted in human femur 302.

Figure 1:
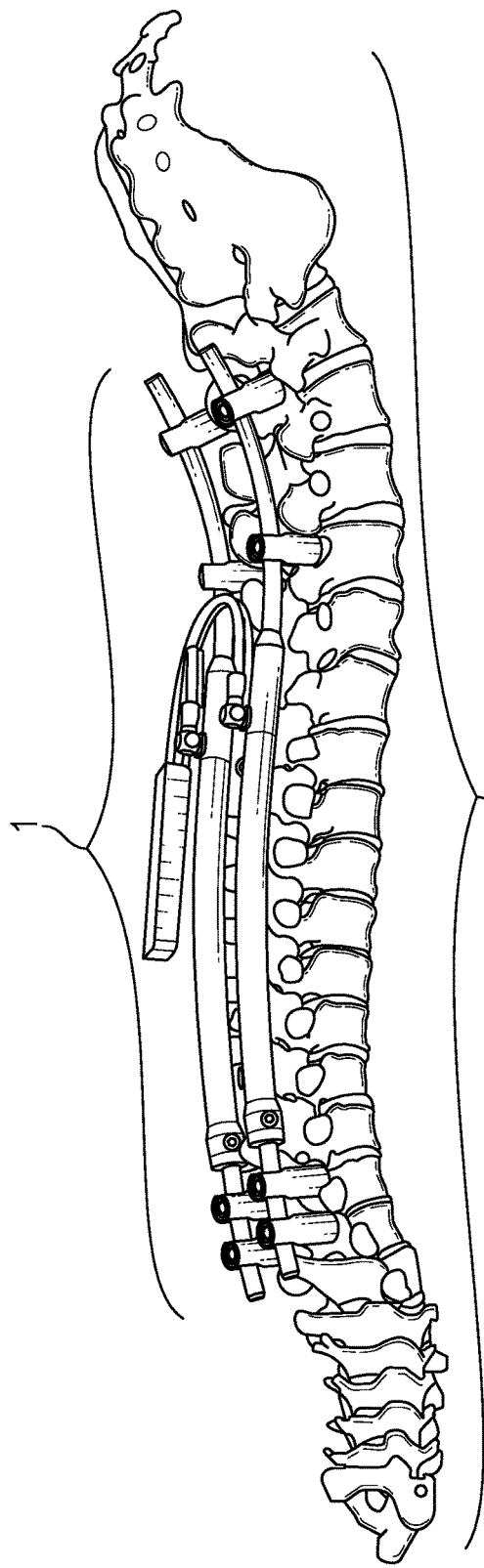
FIG. 1 is a perspective view of a bone implant system according to one embodiment, attached to a spinal column.

It is to be understood that the drawings are for purposes of illustrating the concepts of the present disclosure and may not be drawn to scale. Furthermore, the drawings illustrate exemplary embodiments and do not represent limitations to the scope of the present disclosure.

DETAILED DESCRIPTION

Exemplary embodiments of the present disclosure will be best understood by reference to the drawings, wherein like parts are designated by like numerals throughout. It will be readily understood that the components of the present disclosure, as generally described and illustrated in the drawings, could be arranged, and designed in a wide variety of different configurations. Thus, the following more detailed description of the embodiments of the implants, systems, and methods, as represented in the drawings, is not intended to limit the scope of the present disclosure, but is merely representative of exemplary embodiments of the present disclosure.

The word "exemplary" is used herein to mean "serving as an example, instance, or illustration." Any embodiment described herein as "exemplary" is not necessarily to be construed as preferred or advantageous over other embodiments. While the various aspects of the embodiments are presented in the drawings, the drawings are not necessarily drawn to scale unless specifically indicated.

The following examples have been included to provide guidance to one of ordinary skill in the art for practicing representative embodiments of the presently disclosed subject matter. In light of the present disclosure and the general level of skill in the art, those of skill in the art can appreciate that the following examples are intended to be exemplary only and that numerous changes, modifications, and alterations can be employed without departing from the scope of the presently disclosed subject matter.

Figure 2:
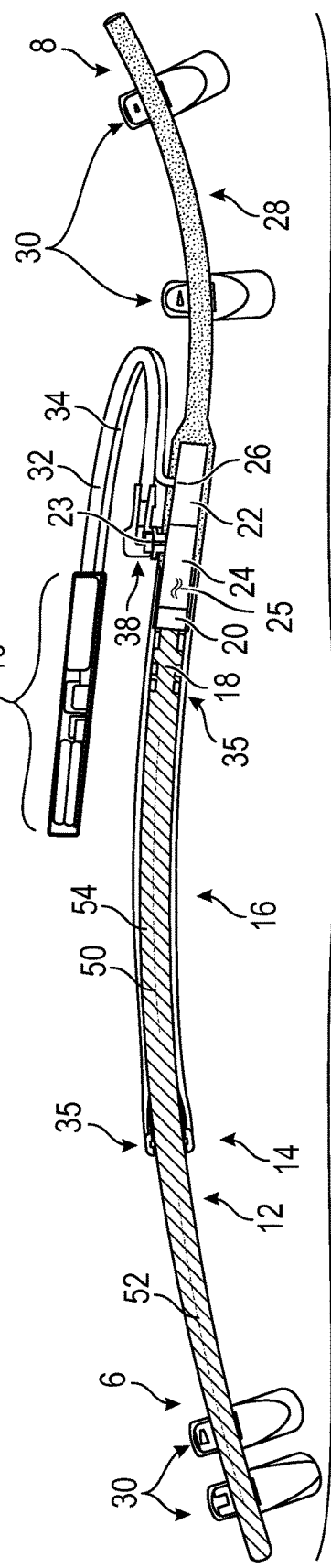
FIG. 2 is a section view of the bone implant system shown in FIG. 1, shown in a contracted length state.

FIG. 1 depicts a bone implant system 1 mounted to a spine 2. Bone implant system 1 may include a single bone implant, or bone implant system 36, as shown in FIG. 2. Alternatively, bone implant system 1 may include two bone implant systems 36 as shown in FIG. 1, and may further include a single, shared sealed unit 10 as shown in FIG. 1 or may include two dedicated sealed units, for example, one sealed unit 10 for each side. Application to the spine 2 is merely exemplary; bone implant systems according to the present disclosure may be used in connection with other bones and/or systems of bones within the body.

FIG. 2 depicts the bone implant system 36 comprised of a superior rod 12, an inferior rod 28, bone anchors 30, sealed unit 10, fluid line 32 and electrical line 34. Superior rod 12 may have superior rod superior end 6 and superior rod inferior end 18, which may include one or more grooves 35 for retaining hydraulic seals, which may be of any type known in the art, such as O-rings (not shown).

In the context of a spine such as the spine 2, bone anchors 30 may be designed to anchor in the spine 2. Thus, bone anchors 30 may be pedicle screws or the like. When used for other bone types, a bone implant system may utilize a different type of bone anchor such as a more conventional bone screw. In other alternative embodiments, bone anchors 30 need not be screws, but can be press-in fasteners, clips, clamps, and/or any other fastener known for securing an implant to bone.

Inferior rod 28 may have inferior rod inferior end 8, inferior rod mid portion 16, and inferior rod superior end 14. Inferior rod superior end 14 may include one or more grooves 35 for retaining hydraulic seals, which may be similar to those used for superior rod inferior end 18. Superior rod 12 and inferior rod 28 may be slidably engaged relative to each other such that superior rod superior end 6 and inferior rod inferior end 8 are able to move apart. More precisely, superior rod 12 and inferior rod 28 may be telescopically engaged with each other such that superior rod inferior end 18 slidably resides in a cavity of inferior rod mid portion 16 (as shown).

Inferior rod mid portion 16 may have a first longitudinal axis 50, which may be curvilinear as shown in FIG. 2, or it may be straight, in order to match the anatomy (or desired future anatomy) of the bone structure to which the bone implant system 36 is applied. Superior rod 12 may have a second longitudinal axis 52 that matches and/or is collinear with the first longitudinal axis 50, at least over the length that the first longitudinal axis 50 and the second longitudinal axis 52 overlap.

In some embodiments, the first longitudinal axis 50 and the second longitudinal axis 52 are both arcuate, with the same radius of curvature, so that the superior rod 12 can move along an arcuate pathway relative to the inferior rod 28. In this application, an "axis" is the geometric center of an elongated member and need not necessarily be rectilinear. Thus, a curved, elongated member may have a curved axis, which may be an arcuate axis extending along an arcuate pathway.

Inferior rod 28 may have an inferior rod internal bore defining an inferior rod cavity 54 extending from inferior rod superior end 14 to some distance along the first longitudinal axis 50. Micropump 24 may optionally be located along the first longitudinal axis 50 and/or the second longitudinal axis 52. This means that micropump 24 may be located such that first longitudinal axis 50 and/or second longitudinal axis 52 passes through micropump 24.

Figure 3:
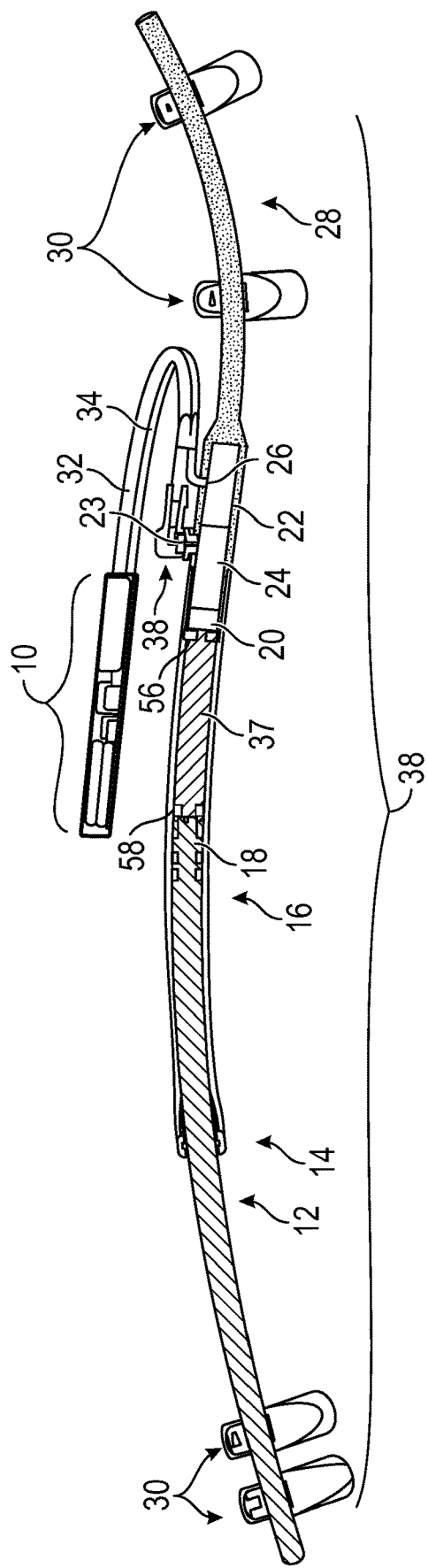
FIG. 3 is a section view of a bone implant system shown in FIG. 1, shown in an extended length state.

More precisely, the micropump 24 may be located at the inferior end of the inferior rod cavity 54. A first chamber 22 may be located immediately inferior to micropump 24 and may house wiring and/or other components related to operation of the bone implant system 36. The micropump 24 may contain a fluid 25. An outlet check valve 20 may be located immediately superior to micropump 24. A second chamber 37 may be located immediately superior to outlet check valve 20, as depicted in FIG. 3. Inlet port 38 may be connected to micropump 24. Inlet check valve 23 may be located inside inlet port 38. Electrical connection 26 may be connected to micropump 24 and pass through first chamber 22.

In this embodiment, micropump 24, first chamber 22, outlet check valve 20, and second chamber 37 may all be located within inferior rod cavity 54. This may help protect the micropump 24, the first chamber 22, the outlet check valve 20, and/or the second chamber 37, and may help streamline and minimize the amount of tissue displaced by the bone implant system 36. Those of skill in the art will recognize that, in alternative embodiments, one or more of these components may be located outside the inferior rod cavity 54. Further, in alternative embodiments, the superior rod 12 may instead have a straight or curved internal bore that receives inferior rod superior end 14, which may be a straight or curved shaft insertable into the internal bore of superior rod 12. In such embodiments, first chamber 22, outlet check valve 20, and/or second chamber 37 may be located within the internal bore of superior rod 12.

FIG. 2 shows bone implant system 36 with a shortened overall length, and FIG. 3 shows bone implant system 36 with a lengthened overall length. Lengthening of bone implant system 36 may be achieved by activating micropump 24 to create a positive displacement of fluid 25, expelling fluid 25 from micropump 24. Use of an incompressible, biocompatible hydraulic fluid, such as mineral oil or silicone oil for the fluid 25, may cause the positive displacement created by the activated micropump 24 to close the inlet check valve 23, open the outlet check valve 20, and cause the fluid 25 to move to second chamber 37, thereby urging the superior rod 12 to move in a superior direction relative to inferior rod 28 in response to pressurization and motion of the fluid 25 into second chamber 37.

Upon activating micropump 24 to assume a contracted volume, outlet check valve 20 may close, inlet check valve 23 may open due to the creation of a negative fluid pressure, and fluid 25 may ingress from fluid line 32 through inlet check valve 23. Thus, micropump 24 may be prepared for further expansion to urge further elongation of the bone implant system 36 as the micropump 24 is driven to expand again. Repeated cycling of micropump 24, in conjunction with the operation of outlet check valve 20 and inlet check valve 23, may provide a ratcheting effect by which bone implant system 36 is driven to elongate in stepwise fashion, without permitting shortening of bone implant system 36. In alternative embodiments, expansion can occur internal to micropump 24 without creating backpressure against inlet check valve 23. In other alternative embodiments, a bone implant system may be configured to shorten if needed, for example, for use with an aging scoliotic patient.

According to one embodiment, micropump 24 is a piezoelectric motor, sometimes referred to as a piezomotor. Due to the piezoelectric effect, applying a charge or voltage to the piezomotor will induce stress in the piezo material, inducing an increase in volume. Removing the charge or voltage reverses the induced stress, resulting in a return to the original volume. Piezo motors appropriate for this application may produce very high stresses in the megapascal range, with very fine length displacements in the micrometer and even nanometer range.

According to one alternative embodiment, micropump 24 is a thermal phase change pump that uses a generally incompressible material that exhibits volume expansion during solid-to-liquid phase transition. For example, paraffin wax provides stable solid-to-liquid phase change behavior resulting in volume expansion ranging from 10-15% with high load-bearing capability. The melting point for paraffin wax is selectable for the application by choosing the appropriate molecular weight of the wax. For this embodiment of the micropump, selecting a melting point 5-10 degrees Celsius above body temperature may be sufficient to ensure that body temperature fluctuations would not activate the phase change, and low enough not to cause thermal damage to surrounding body tissues. Other types of micropumps or motors may be usable, as would be anticipated by a person skilled in the art with the aid of the present disclosure.

The foregoing are only examples—in other embodiments, micropump 24 may be any type of pump known in the art that is capable of providing low displacement. In the present disclosure, a "micropump" is a device that uses an expanding and/or contracting element to provide fluid motion, and provides fluid displacement within the range of one to ten microliters per pump cycle (e.g., per expansion and/or contraction cycle). Expansion/contraction cycles may occur according to any desired schedule. According to some examples, the micropump 24 may undergo one expansion/contraction cycle per day, resulting in a very gradual elongation of the bone implant system 36.

Use of a micropump may have several benefits, including the ability to use a smaller pump that can provide a high mechanical advantage in a small volume. This may enable placement of a pump within the envelope defined by the superior rod 12 and the inferior rod 28 and/or on the longitudinal axis of the superior rod 12 and/or of the inferior rod 28. This positioning may provide a simple design and avoid the need to displace additional tissues within the body. Further, a micropump may have few moving parts, enhancing reliability and cost-effectiveness. Use of a micropump is merely exemplary. Those of skill in the art will recognize that other types of pumps may be used within the scope of the present disclosure.

Figure 4:
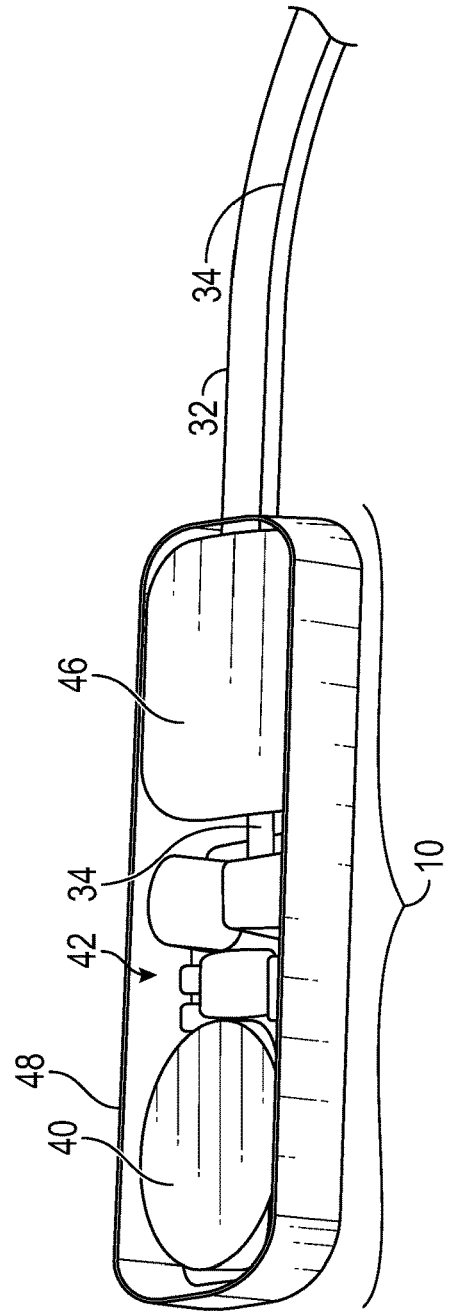
FIG. 4 is a perspective view of the interior of a sealed unit of the bone implant system shown in FIG. 2 and FIG. 3.

FIG. 4 shows an inside view of sealed unit 10, with the one side removed. Sealed unit 10 may have a housing 48 containing battery 40, circuit board 42, and fluid reservoir 46. Sealed unit 10 may be hermetically sealed to ensure that there is no contact between its internal components and the surrounding body tissues. Fluid line 32 and electrical line 34 may extend from sealed unit 10. Fluid line 32 may be connected to fluid reservoir 46, and electrical line 34 may be connected to circuit board 42.

Circuit board 42 may be a control system that is configured to control operation of the micropump 24, thus controlling elongation of the bone implant system 36. Circuit board 42 may thus include various electronic components that provide the appropriate electrical signal to activate and deactivate micropump 24. Circuit board 42 may further include a wireless communication device, such as Bluetooth or wi-fi transceiver, to facilitate wireless communication with the bone implant system 36 from a location outside the body but within range of the wireless transceiver. For example, the bone implant system 36 could be controlled by a computer application running on a smartphone or other computing device, which may communicate with circuit board 42 with corresponding wireless communication hardware. Thus, medical professionals may control operation of bone implant system 36 without the need to surgically access the sealed unit 10, or any other part of bone implant system 36.

Furthermore, circuit board 42 may further include componentry necessary for interpreting signals from one or more sensors embedded in the bone implant system 36. For example, a pressure sensor 56 (shown in FIG. 3) may be located in second chamber 37, and the pressure reading from the pressure sensor 56 may be used to calculate the force urging the superior rod 12 to move in a superior direction relative to inferior rod 28.

As another alternative, a displacement sensor 58 such as a Hall effect sensor, linear variable displacement transducer (LVDT), or other displacement sensor may be used to detect the relative linear displacement between the superior rod 12 and the inferior rod 28. Displacement sensor 58 may be located within the second chamber 37, or at another location suitable for displacement measurement.

Circuit board 42 may receive sensor data from pressure sensor 56, displacement sensor 58, and/or one or more other sensors that monitor other aspects of the operation of the bone implant system 36. In some embodiments, circuit board 42 may be configured to automatically actuate micropump 24 to elongate the bone implant system 36. For example, sensor data from pressure sensor 56 may indicate the presence of elongating force exerted on the bone implant system 36 by the spine to which it is attached, indicating that growth in the spine has occurred. In response, circuit board 42 may trigger elongation of bone implant system 36 via activation of micropump 24.

Figure 5:
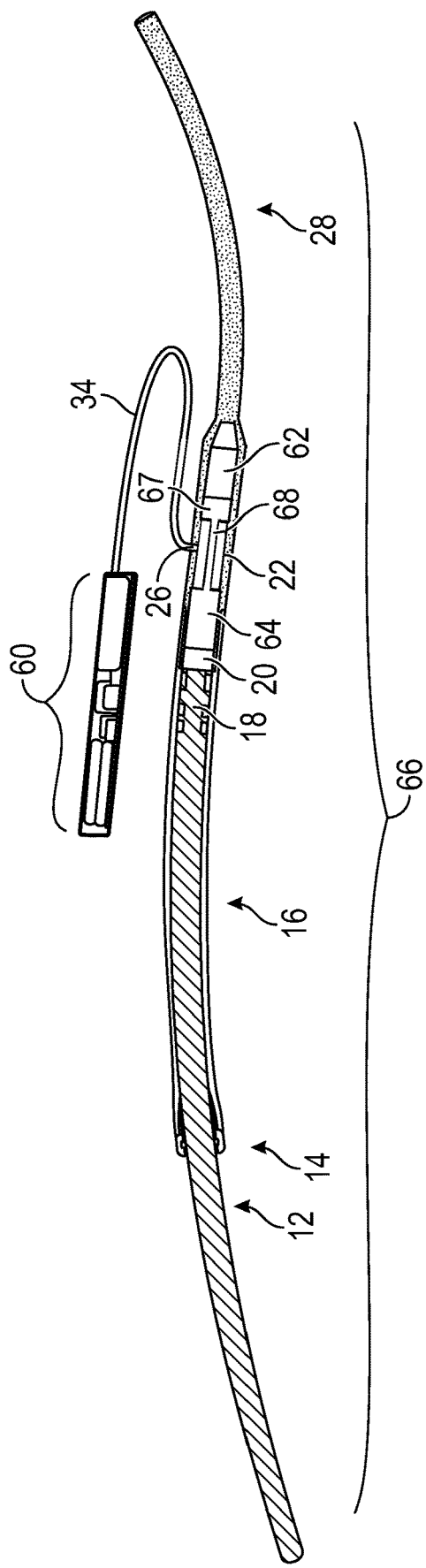
FIG. 5 is a section view of an alternative embodiment of a bone implant system.

FIG. 5 shows a bone implant system 66 according to one alternative embodiment. Bone implant system 66 may have a fluid reservoir 62 which is located immediately inferior to an inlet check valve 67, which may be located inferior to micropump 64. First chamber 22 may have a central channel 68 that provides fluid communication between inlet check valve 67 and micropump 64. When micropump 64 expands in volume as described previously, it may cause the inlet check valve 67 to close, causing outlet check valve 20 to open and causing fluid 25 to move from fluid reservoir 62 to second chamber 37 (as shown in FIG. 3), thereby urging the superior rod 12 to move in a superior direction relative to the inferior rod 28.

When micropump 64 returns to its original volume as described previously, it may cause the inlet check valve 67 to open, causing the outlet check valve 20 to close, and causing fluid 25 to move from fluid reservoir 62 to micropump 64. By repeating the expansion-contraction cycle of the micropump, incremental lengthening of the overall length of bone implant system 66 may achieved. Micropump 64 may be connected to sealed unit 60 by electrical line 34 at electrical connection 26.

Figure 6:
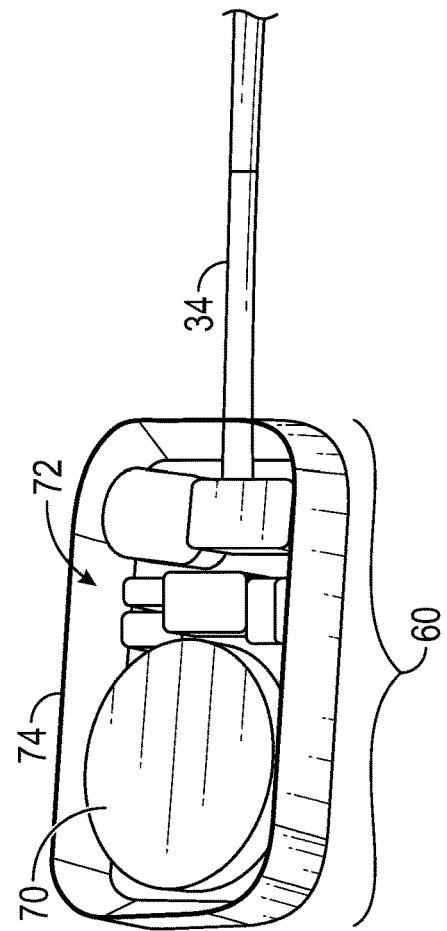
FIG. 6 is a perspective view of the interior of a sealed unit of the bone implant system shown in FIG. 5.

FIG. 6 depicts an inside view of sealed unit 60, with the one side removed. Sealed unit 60 may have a housing 74 containing battery 70 and circuit board 72. Sealed unit 60 may be hermetically sealed to ensure that there is no contact between its internal components and the surrounding body tissues. Electrical line 34 may extend from sealed unit 60 and may be connected to circuit board 72. Circuit board 72 may operate as a control system by controlling operation of micropump 64. Thus, circuit board 72 may have various electronic components that provide the appropriate electrical signal to activate and deactivate micropump 64. As explained previously for circuit board 42, circuit board 72 may further comprise a wireless communication component, such as Bluetooth or wi-fi transceiver.

Figure 7:
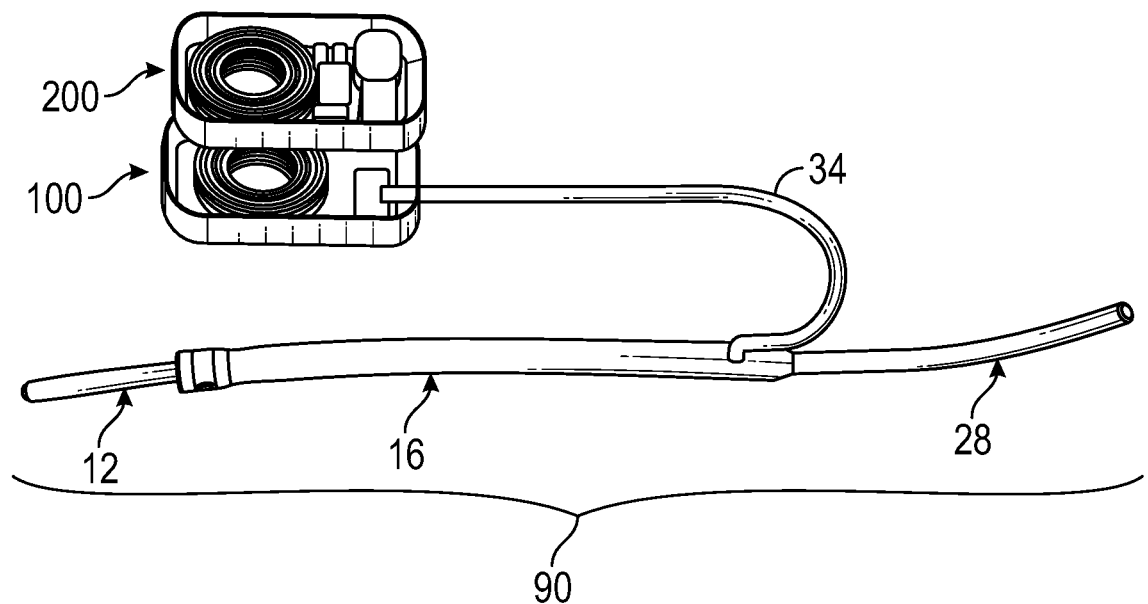
FIG. 7 is a perspective view of an alternative embodiment of a bone implant system.
Figure 8:
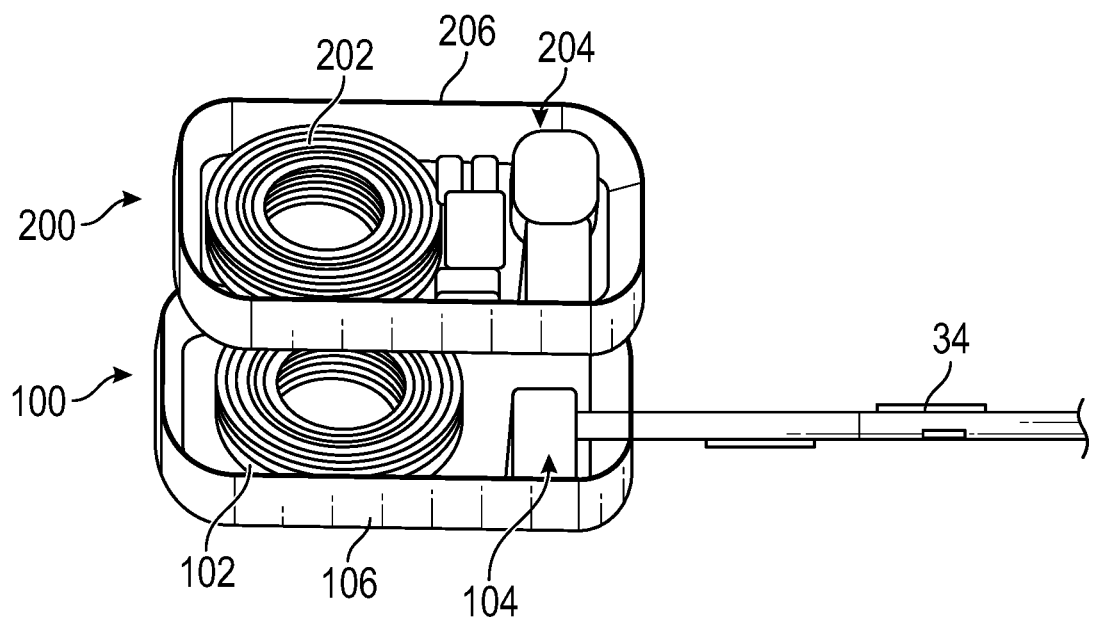
FIG. 8 is a perspective view of the interior of two sealed units of the bone implant system shown in FIG. 7.

FIG. 7 is a perspective view of a bone implant system 90 according to another alternative embodiment. Bone implant system 90 may have a section view similar to the section views depicted in FIG. 2, FIG. 3, and/or FIG. 5. Electrical line 34 may be connected to first sealed unit 100. First sealed unit 100 is configured to be implanted in a subcutaneous location in the body, or just below the skin. Control unit 200 may be placed immediately above the skin and generally aligned with first sealed unit 100 just below the skin. First sealed unit 100 may have a housing 106 containing first inductive coil 102 and circuit board 104. Control unit 200 may have a second housing 206 containing second inductive coil 202 and second circuit board 204. Control unit 200 may be connected to a power supply (not shown). By causing current flow in second induction coil 202, control unit 200 may induce current flow in first induction coil 102, thereby transmitting the needed electrical energy to control the micropump 24 or micropump 64, and any other necessary electronics in a wireless, non-contact manner. In alternative embodiments, the first inductive coil 102 and the second inductive coil 202 may be configured to transmit data to or from the circuit board 104, and may thus perform the function of the wireless communication device referenced above.

Thus, first sealed unit 100 may be operable without containing a battery or other internal power source. Additionally or alternatively, instructions for operation of bone implant system may be transferred inductively from second induction coil 202 to first induction coil 102. Thus, medical professionals may trigger elongation of bone implant system 90 without the need to surgically access the first sealed unit 100.

Bone implant systems according to the present disclosure may be used for a wide variety of bone types and applications. The bone implant systems shown and described in connection with FIGS. 1-8 are for spinal use; however, in alternative embodiments, the principles of the present disclosure may be applied to other bones to provide structural support while enabling elongation. For example, a pediatric intramedullary nail may be used to support a fractured or weakened bone while allowing growth in the bone to occur. One such example will be shown and described in connection with FIGS. 9-11.

FIG. 9 depicts a bone implant system 336 mounted in a human femur 302. The superior portion of the human femur 302 is on the left side of the page, as in FIGS. 10 and 11 in which the superior side is also on the left.

FIG. 10 is a partial cutaway view of the bone implant system 336 mounted in human femur 302 with bone growth 304 depicted as a gap, wherein bone would grow during the expansion of a bone implant system 336. Bone implant system 336 may have a proximal rod 312, a distal rod 328, and bone anchors 330 that secure the proximal rod 312 and the distal rod 328 to the proximal and distal portions of the human femur 302, respectively. The proximal rod 312 and the distal rod 328 may cooperate to define an intramedullary nail of adjustable length.

Figure 11:
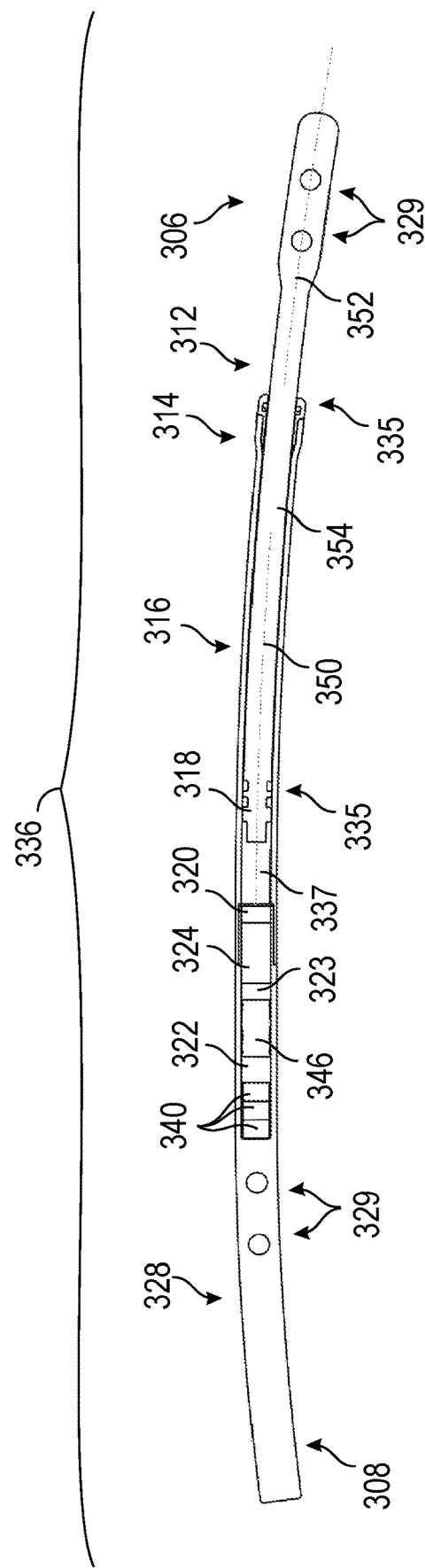
FIG. 11 is a section view of the bone implant system of FIG. 9.

FIG. 11 is a section view of bone implant system 336. Proximal rod 312 may have proximal rod proximal end 306 and proximal rod distal end 318, which may include one or more grooves 335 for retaining hydraulic seals, which may be of any type known in the art, such as O-rings (not shown).

Distal rod 328 may have distal rod distal end 308, distal rod mid portion 316, and distal rod proximal end 314. Distal rod proximal end 314 may include one or more grooves 335 for retaining hydraulic seals, which may be similar to those used for proximal rod distal end 318. Proximal rod 312 and distal rod 328 may be slidably engaged relative to each other such that proximal rod proximal end 306 and distal rod distal end 308 are able to move apart. More precisely, proximal rod 312 and distal rod 328 may be telescopically engaged with each other such that proximal rod distal end 318 slidably resides in a cavity of distal rod mid portion 316 (as shown).

Distal rod distal end 308 and proximal rod proximal end 306 may be fitted with one or more mount holes 329 sized to accept bone anchors 330.

Distal rod mid portion 316 may have a first longitudinal axis 350, which may be curvilinear as shown in FIG. 11, or it may be straight, in order to match the anatomy (or desired future anatomy) of the bone structure to which the bone implant system 336 is applied. Proximal rod 312 may have a second longitudinal axis 352 (not shown) that matches and/or is collinear with the first longitudinal axis 350, at least over the length that the first longitudinal axis 350 and the second longitudinal axis 352 overlap.

In some embodiments, the first longitudinal axis 350 and the second longitudinal axis 352 are both arcuate, with the same radius of curvature, so that the proximal rod 312 can move along an arcuate pathway relative to the distal rod 328.

Distal rod 328 may have a distal rod internal bore defining a distal rod cavity 354 extending from distal rod proximal end 314 to some distance along the first longitudinal axis 350. Micropump 324 may optionally be located along the first longitudinal axis 350 and/or the second longitudinal axis 352. This means that micropump 324 may be located such that first longitudinal axis 350 and/or second longitudinal axis 352 passes through micropump 324.

More precisely, the micropump 324 may be located at the distal end of the distal rod cavity 354, immediately distal to outlet check valve 320. An inlet check valve 323 may be situated between micropump 324 and fluid reservoir 346. Actuating micropump 324 may pressurize fluid through outlet check valve 320 to second chamber 337, thereby urging distal rod 328 to move in a proximal direction relative to distal rod 328 in response to pressurization and motion of the fluid into second chamber 337.

A first chamber 322 may be located immediately distal to fluid reservoir 346 and may contain electronics necessary for wireless communications or drive circuitry needed for micropump 324 or any sensors. Bone implant system 336 may be powered in any manner previously mentioned or in any other manner that would be recognized by a person skilled in the art with the aid of the present disclosure, or by one or more batteries 340. FIG. 11 shows three batteries, by way of example.

In this embodiment, micropump 324, outlet check valve 320 inlet check valve 323, fluid reservoir 346, first chamber 322, battery 340, and second chamber 337 may all be located within distal rod cavity 354. Those of skill in the art will recognize that one or more of these components may be located outside the distal rod cavity 354. Further, in alternative embodiments, the proximal rod 312 may instead have a straight or curved internal bore that receives distal rod proximal end 314, which may be a straight or curved shaft insertable into the internal bore of proximal rod 312. In such embodiments, micropump 324, outlet check valve 320 inlet check valve 323, fluid reservoir 346, first chamber 322, battery 340, and/or second chamber 337 may be located within the internal bore of proximal rod distal end 318.

The operation of bone implant system 336 may be similar to that of the bone implant systems of FIGS. 1-8. The micropump 324 may be actuated continuously or intermittently to gradually induce elongation of the bone implant system 336. The outlet check valve 320 may restrict fluid backflow back through the micropump 324 to restrict reduction in the length of the bone implant system 336. Thus, the bone implant system 336 may provide structural support to the human femur 302 while permitting growth of the human femur 302.

Reference throughout this specification to "an embodiment" or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, figure, or description thereof for the purpose of streamlining the present disclosure. This method of disclosure, however, is not to be interpreted as reflecting an intention that any embodiment requires more features than those expressly recited in that embodiment. Rather, inventive aspects lie in a combination of fewer than all features of any single foregoing disclosed embodiment.

As used herein, the term "proximal" means a location relatively closer to a user (i.e., a surgeon) when the user is installing the implant. The term "distal" means a location relatively further from the user. For example, when a user installs a bone screw into a material with a driver, the end of the bone screw engaged with the driver is the proximal end, and the tip of the bone screw that first engages the material is the distal end. As used herein, the term "superior" means a location relatively closer to a head, the term "inferior" means location relatively farther away from a head.

Recitation of the term "first" with respect to a feature or element does not necessarily imply the existence of a second or additional such feature or element. Elements recited in means-plus-function format are intended to be construed in accordance with 35 U.S.C. § 112(f). It will be apparent to those having skill in the art that changes may be made to the details of the above-described embodiments without departing from the underlying principles set forth herein.

The phrases "connected to," "coupled to" and "in communication with" refer to any form of interaction between two or more entities, including mechanical, electrical, magnetic, electromagnetic, fluid, and thermal interaction. Two components may be functionally coupled to each other even though they are not in direct contact with each other. The term "coupled" can include components that are coupled to each other via integral formation, as well as components that are removably and/or non-removably coupled with each other. The term "abutting" refers to items that may be in direct physical contact with each other, although the items may not necessarily be attached together. The phrase "fluid communication" refers to two or more features that are connected such that a fluid within one feature is able to pass into another feature. As defined herein the term "substantially" means within +/−20% of a target value, measurement, or desired characteristic.

While specific embodiments and applications of the present disclosure have been illustrated and described, it is to be understood that the scope of this disclosure is not limited to the precise configuration and components disclosed herein. Various modifications, changes, and variations which will be apparent to those skilled in the art may be made in the arrangement, operation, and details of the devices, systems, and methods disclosed herein.

The invention claimed is:

1. A bone implant system comprising:
a plurality of bone anchors;
a superior rod configured to be attached to a superior portion of a bone via the bone anchors, the superior rod comprising a superior end;
an inferior rod configured to be attached to an inferior portion of the bone via the bone anchors, the inferior rod comprising an inferior end, wherein the inferior rod is movably coupled to the superior rod such that a length of the combined superior and inferior rods, measured between the superior end and the inferior end, is adjustable;
a chamber; and
a micropump configured to urge fluid to flow into the chamber to cause the length to increase;
wherein the micropump is configured to provide a fluid displacement within the range of one to ten microliters per pump cycle such that the bone implant system is configured to be secured to a human spine to increase the length by an increment suitable for a daily elongation cycle;
wherein the superior rod and the inferior rod are slidably coupled together in a manner that permits adjustment of the length without any threaded interface between the superior rod and the inferior rod; wherein: the superior rod telescopically engages the inferior rod such that a cavity is present within at least one of the superior rod and the inferior rod; the chamber is within the cavity; and the micropump is within the cavity.

2. The bone implant system of claim 1, wherein the micropump comprises one of:
a piezoelectric motor; and
a thermal phase change pump.

3. The bone implant system of claim 1, further comprising an outlet check valve configured to:
permit flow of the fluid from the micropump to the chamber; and
restrict flow of the fluid from the chamber to the micropump.

4. The bone implant system of claim 3, further comprising:
a reservoir; and
an inlet check valve configured to:
permit flow of the fluid from the reservoir to the micropump; and
restrict flow of the fluid from the micropump to the reservoir.

5. The bone implant system of claim 1, further comprising a control system, operatively connected to the micropump, that is configured to control operation of the micropump.

6. The bone implant system of claim 5, wherein the control system comprises a wireless communication device configured to perform at least one of transmitting and receiving wireless signals.

7. The bone implant system of claim 5, further comprising a sensor operatively connected to provide sensor data to the control system;
wherein the control system is configured to control the micropump based on the sensor data.

8. The bone implant system of claim 7, wherein the sensor data is indicative of at least one of:
a pressure of the fluid; and
a displacement of the superior rod relative to the inferior rod.

9. The bone implant system of claim 1, wherein the inferior rod is movably coupled to the superior rod such that the superior rod moves along an arcuate pathway relative to the inferior rod.

10. The bone implant system of claim 1, wherein:
an axis extends between the superior end and the inferior end; and
the superior rod and the inferior rod are further coupled together in a manner that permits adjustment of the length via translation along the axis without relative rotation between the superior rod and the inferior rod.

11. The bone implant system of claim 10, wherein the chamber is further configured to elongate along the axis in response to fluid flow into the chamber to cause the length to increase.

12. A bone implant system comprising:
a plurality of bone anchors;
a superior rod configured to be attached to a superior portion of a bone via the bone anchors, the superior rod comprising a superior end;
an inferior rod configured to be attached to an inferior portion of the bone via the bone anchors, the inferior rod comprising an inferior end, wherein the inferior rod is movably coupled to the superior rod such that a length of the combined superior and inferior rods, measured along an axis between the superior end and the inferior end, is adjustable;
a chamber; and
a pump configured to urge fluid to flow into the chamber to cause the length to increase;
wherein:
one of the superior rod and the inferior rod contains the chamber;
the other of the superior rod and the inferior rod is devoid of an interior cavity;
the superior rod and the inferior rod are slidably coupled together in a manner that permits adjustment of the length via sliding translation along the axis without any threaded interface between the superior rod and the inferior rod; the superior rod telescopically engages the inferior rod such that a cavity is present within at least one of the superior rod and the inferior rod; the chamber is positioned within the cavity; and the pump is within the cavity.

13. The bone implant system of claim 12 wherein the pump comprises a micropump that comprises one of:
a piezoelectric motor; and
a thermal phase change pump.

14. The bone implant system of claim 12, further comprising an outlet check valve configured to:
permit flow of the fluid from the pump to the chamber; and
restrict flow of the fluid from the chamber to the pump.

15. The bone implant system of claim 14, further comprising:
a reservoir; and
an inlet check valve configured to:
permit flow of the fluid from the reservoir to the pump; and
restrict flow of the fluid from the pump to the reservoir.

16. The bone implant system of claim 12, further comprising a control system, operatively connected to the pump, that is configured to control operation of the pump.

17. The bone implant system of claim 16, wherein the control system comprises a wireless communication device configured to transmit, receive, or transmit and receive wireless signals.

18. The bone implant system of claim 16, further comprising a sensor operatively connected to provide sensor data to the control system;
wherein the control system is configured to control the pump based on the sensor data.

19. The bone implant system of claim 18, wherein the sensor data is indicative of at least one of:
a pressure of the fluid; and
a displacement of the superior rod relative to the inferior rod.

20. The bone implant system of claim 12, wherein the inferior rod is movably coupled to the superior rod such that the superior rod moves along an arcuate pathway relative to the inferior rod.

21. A bone implant system comprising:
a plurality of bone anchors;
a superior rod configured to be attached to a superior portion of a bone via the bone anchors, the superior rod comprising a superior end;
an inferior rod configured to be attached to an inferior portion of the bone via the bone anchors, the inferior rod comprising an inferior end, wherein the inferior rod is movably coupled to the superior rod such that a length of the combined superior and inferior rods, measured along an axis between the superior end and the inferior end, is adjustable;
a chamber;
a pump configured to urge fluid to flow into the chamber such that the chamber elongates along the axis to cause the length to increase;
wherein:
one of the superior rod and the inferior rod comprises a first curvature; and
one of the superior rod and the inferior rod comprises a hollow portion containing the chamber; and the hollow portion comprises one of a straight longitudinal axis and a second curvature different from the first curvature; the superior rod and the inferior rod are slidably coupled together in a manner that permits adjustment of the length without any threaded interface between the superior rod and the inferior rod; the superior rod telescopically engages the inferior rod such that a cavity is present within at least one of the superior rod and the inferior rod; and the pump and the chamber are within the cavity.

22. The bone implant system of claim 21, further comprising:
a reservoir;
an inlet check valve configured to:
permit flow of the fluid from the reservoir to the pump; and
restrict flow of the fluid from the pump to the reservoir; and
an outlet check valve configured to:
permit flow of the fluid from the pump to the chamber; and
restrict flow of the fluid from the chamber to the pump.

23. The bone implant system of claim 21, further comprising a control system, operatively connected to the pump, that is configured to control operation of the pump;
wherein the control system comprises a wireless communication device configured to transmit, receive, or transmit and receive wireless signals.

24. The bone implant system of claim 21, wherein:
the inferior rod is movably coupled to the superior rod such that the superior rod moves along an arcuate pathway relative to the inferior rod.

25. The bone implant system of claim 24, wherein the pump comprises a micropump that comprises one of:
a piezoelectric motor; and
a thermal phase change pump.

* * * * *